United States Patent [19]

Lodhi et al.

[11] 4,211,793

[45] Jul. 8, 1980

[54] TRIETHYL CITRATE SOLUTIONS OF PGE-TYPE COMPOUNDS

[75] Inventors: Shahid A. Lodhi, Spring Valley; Bernard Sims, Monsey, both of N.Y.

[73] Assignee: American Cyanamid Company, Stamford, Conn.

[21] Appl. No.: 21,859

[22] Filed: Mar. 19, 1979

[51] Int. Cl.$^2$ ............... A61K 31/215; A61K 31/225; A61K 31/19

[52] U.S. Cl. .................................. 424/305; 424/313; 424/317

[58] Field of Search ..................... 424/305, 317, 313

[56] References Cited

PUBLICATIONS

Chem. Abst. 9th Coll. Index, vol. 76–85, (1972–1976), p. 31214cs.

Primary Examiner—Sam Rosen
Attorney, Agent, or Firm—Norton S. Johnson

[57] ABSTRACT

Degradation of E-type prostaglandin compounds is prevented by dissolving those compounds in triethyl citrate.

5 Claims, No Drawings

TRIETHYL CITRATE SOLUTIONS OF PGE-TYPE COMPOUNDS

BACKGROUND OF THE INVENTION

Prostaglandins are a group of closely related carboxylic acids containing a cyclopentane ring with two adjacent carbon side chains, one of which bears the carboxyl group at the terminal position. Most of the naturally occurring prostaglandins may be regarded as derivatives of the parent structure prostenoic acid. Natural prostaglandins are divided into four groups and although these may be named in accordance with their relationship to prostenoic acid, they are more conveniently referred to by the letters A, B, E, and F (shown below): all four groups have in common a trans=13,14 position bond, and a hydroxyl group at $C_{15}$.

sives, antilipodemics, bronchodilators, fertility control agents, and gastric secretion inhibitors. Bergstrom, et al., Pharmacol. Rev. (20), 1, 1968, and the references cited therein. See also, U.S. Pat. Nos. 3,069,322 and 3,598,858 concerning esters of prostaglandins of the E-type. The basic problem in the pharmacological utilization of these drugs occurs in the relatively unstable nature of prostanglandin-like compounds of the E-type in conventional pharmaceutical formulations. These compounds tend to decompose, at and above room temperature, and in the presence of small amounts of acid or base. For example, $PGE_2$ changes to $PGA_2$ in the presence of acid, while $PGE_2$ changes to $PGB_2$ in the presence of base. Similarly, other prostaglandin-like compounds of the E-type change to their corresponding compounds of the A- and B-type. In general, it can be said that the E-type prostaglandins may be distin-

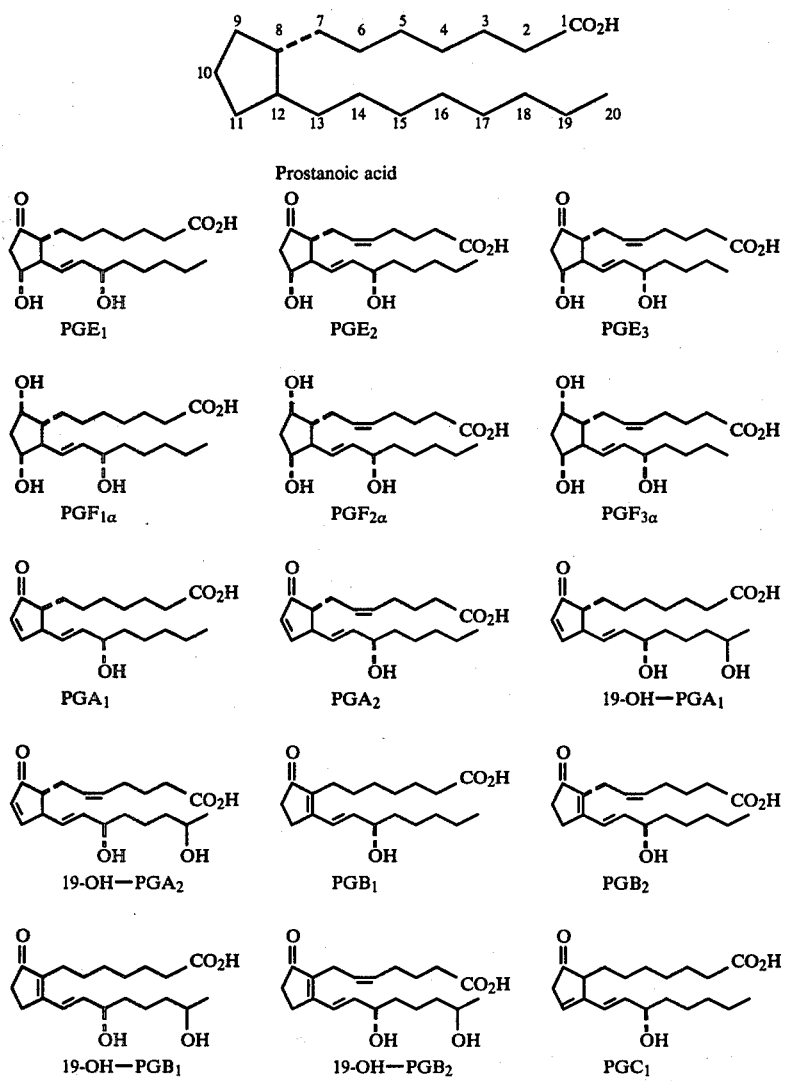

Further, the E- and F-type possess an additional hydroxyl at $C_{11}$, with the E-type bearing a carbonyl function at $C_9$ while the F-type bears an hydroxyl at $C_9$.

Prostaglandins of the E-type and their esters are extremely potent in causing various biological responses and, for this reason, are useful for pharmacological purposes. Among these purposes are use as hypotenguished from A- and B-type prostaglandins by the presence of a hydroxyl at $C_{11}$ (shown below), and the A and B types may be regarded as dehydration products of E-type compounds resulting from a removal of the $C_{11}$ hydroxyl and the formation of a double bond in the ring.

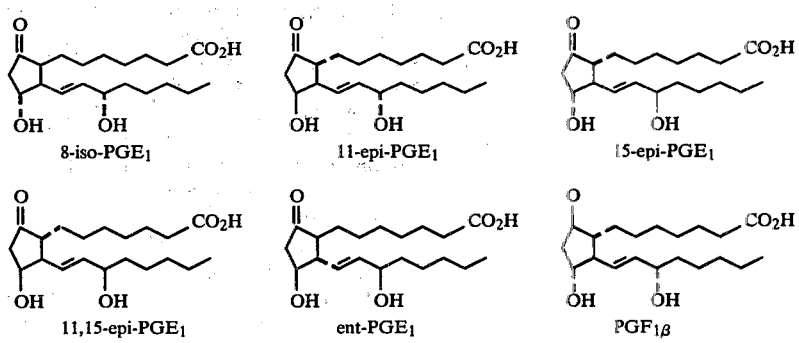

Even in neutral aqueous solution or in a neat state there is a gradual change for E-types to A-types and B-types. Stability of the E-types has been observed in some solutions and in solid form at −20° C. or lower but storage at this temperature is impractical and administration to mammals practically impossible. Better success at stabilizations have been obtained with other solutions and compositions as described in U.S. Pat. Nos. 3,749,800; 3,826,823; 3,829,579 and 3,851,052 and by Srivastava et al., Lipids, (8), 592 (1973), wherein ethyl acetate, chloroform, and ethanol are used as solvents for prostaglandins of the E-types. Such solvents, however, are unsuitable for pharmaceutical dosage forms without dilution with water which causes rapid decomposition. A quantization of such decomposition may be found in Table I. The essence of the present invention resides in the discovery that prostaglandins and prostaglandin-like compounds of the E-type can be dissolved in the normally liquid substance known as triethyl citrate to provide an unexpectedly stable and useful pharmaceutical dosage form for the direct administration to warm-blooded animals. Prostaglandin stabilized by triethyl citrate of the present invention is particularly adaptable for oral administration of therapeutic doses of prostaglandins.

SUMMARY OF THE INVENTION

Triethyl citrate of the formula:

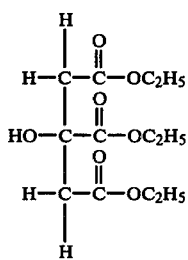

is an oily liquid having a density at 20° C. 1.37 and a viscosity (at 25° C. of 35.2 centipoise) and a pour point of about 10° C. Additions of prostaglandin E-types to triethyl citrate will serve to prevent or greatly retard the normal conversion by dehydration of prostaglandin E-types to prostaglandins of the A-type and B-type. The following non-limiting examples will describe the ability of triethyl citrate to retard the degradation and dehydration of prostaglandin E-type in its broadest aspects initially and will progress to more specific examples.

The broadest embodiment of the invention involves taking the desired E-type prostaglandin, dissolving it in triethyl citrate at concentrations of 2.5 to 20 milligrams per ml. thus forming a clear solution. These solutions exhibit excellent stability during storage at 70° C. Table I shows that after six days there was less than 2 percent degradation of the prostaglandin E-type compound. During the same period, the control [Table I] underwent 95% degradation of the prostaglandin E-type compound. The degradation products of the E-type prostaglandin were largely to the A and B type prostaglandins. In the general case, preservation of the prostaglandin E-type in the present invention is accomplished by adding the prostaglandin of the E-type to the triethyl citrate at the desired concentration of prostaglandin E-type and the mixture is stirred at room temperature until the homogeneous solution is obtained.

EXAMPLE 1

To 5 ml. of triethyl citrate at 25° C. is added from about 1.0 to $10^3$ micrograms of 16,16-dimethyl-$PGE_2$. The mixture is stirred with a blade-type stirrer for 15 minutes until a homogeneous solution is obatined.

EXAMPLE 2

Utilizing the procedure of Example one substitute 15-methyl-$PGE_2$ for 16,16-dimethyl-$PGE_2$.

EXAMPLE 3

Utilizing the procedure of Example 1, substituting for 16,16-dimethyl-$PGE_2$, 15R,15-methyl-$PGE_2$ or their methyl esters are added in concentrations of about 1 microgram to $10^3$ micrograms per milliliter of triethyl citrate and stirring with the blade type stirrer until a homogeneous solution is obtained.

EXAMPLE 4

The product of Claim 1 may be utilized in an oral dosage form by adding the homogeneous triethyl citrate/PGE mixture to a soft-shelled gelatin capsule prepared by art recognized methods. The above-mentioned compounds in a variety of concentrations are then typically administered for the reduction of gastric secretion and the prevention or healing of peptic ulcers in humans, or other therapeutic uses of prostaglandins.

It is an object of this invention to preserve for storage purposes prostaglandins of the E-type.

Further, it is an object of this invention to prevent the degradation of E-type prostaglandins.

It is a further object of this invention to prevent dehydration of E-type prostaglandins.

It is a further object of this invention to prevent or retard the conversion of E-type prostaglandins to A- or B-type prostaglandins.

It is another object of this invention to prepare prostaglandins of the E-type in a form suitable for oral administration without the anticipated loss of potency due to the rapid decomposition of E-type prostaglandins. It will occur to those skilled in the art that other utilization of the above invention may be made without departing from the spirit and intent of this invention. The aforementioned examples are merely illustrative of the intended invention and are in no way expressly limiting the invention. The invention is limited solely by the claims.

TABLE I

| | Percent E-type Prostaglandin degraded* | |
|---|---|---|
| Time (days) | Control | Triethyl citrate |
| 0 | 0% | 0% |
| 2 | 45% | not detectable |
| 4 | 80% | not detectable |
| 6 | | 1-2% |
| 14 | | 5-10% |

*70° C.

We claim:

1. A method for preserving the E-type prostaglandins during storage by dissolving the E-type prostaglandins in triethyl citrate.

2. A stable mixture of prostaglandins of the E-type suitable for oral administration by the admixture of prostaglandins of the E-type in solution with triethyl citrate.

3. A stable mixture of E-type prostaglandins in triethyl citrate according to the product of claim 2 wherein said solution contains said prostaglandins in concentration from about 1 microgram to about $10^3$ microgram/milliliter of triethyl citrate.

4. A stable dosage form according to claim 2 wherein said solution is contained in a capsule of a pharmaceutically acceptable water dispersible material.

5. A stable dosage form according according to claim 4 wherein said material contains gelatin and the capsule is soft and elastic.

* * * * *